United States Patent [19]

Heimer et al.

[11] Patent Number: 4,772,547

[45] Date of Patent: Sep. 20, 1988

[54] HTLV-III ENVELOPE PEPTIDES

[75] Inventors: Edgar P. Heimer, Sparta; Premkumar E. Reddy, Montclair, both of N.J.; Robert C. Gallo; Flossie Wong-Staal, both of Bethesda, Md.

[73] Assignees: Hoffmann-La Roche Inc., Nutley, N.J.; United States of America, Washington, D.C.

[21] Appl. No.: 824,913

[22] Filed: Feb. 3, 1986

[51] Int. Cl.[4] ..................... C07K 7/10; G01N 33/545; G01N 33/577; C12Q 1/70

[52] U.S. Cl. .......................................... 435/5; 424/86; 435/7; 435/68; 435/172.1; 435/240.27; 435/805; 435/810; 436/548; 436/811; 436/531; 530/324; 530/325; 530/326; 530/327; 530/387; 530/806; 530/807; 530/808

[58] Field of Search ...................... 435/517, 68, 172.1, 435/240, 805, 810, 240.27; 436/548, 811, 531; 424/86; 530/324-327, 387, 806-808

[56] References Cited

U.S. PATENT DOCUMENTS

| | | | |
|---|---|---|---|
| 4,520,113 | 5/1985 | Gallo et al. | 436/504 |
| 4,591,552 | 5/1986 | Neurath | 436/534 |
| 4,629,783 | 12/1986 | Cosand | 530/324 |

OTHER PUBLICATIONS

Meusing et al., "Nucleic Acid Structure and Expression of the Human AIDS/Lymphadenopathy Retrovirus", Nature 313 (2/7/85) 450-8.

Veronese et al., "Characterization of GP41 as the Transmembrane Protein Coded by the HTLV-III/-LAV Envelope Gene", Science 229 (9/27/85) 1402-5.

Pavletti et al., "Application of a Modified Computor Algorithm in Determining Potential Antigenic Determinents Associated with the AIDS Virus Glycoprotein", Analytical Biochemistry, 151 (12/85) 540-6.

Cabradilla et al., "Serodiagnosis of Antibodies to the Human AIDS Retrovirus with a Baterially Synthesized Env Polypeptide", Bio/Technology, 4 (2/86) 128-133.

Chang et al., "Expression of *Escherichia coli* of Open Reading Frame Gene Segments of HTLV-III, Science 228 (4/5/85) 93-6.

Chang et al., "Detection of Antibodies to Human T--Cell Lymphotropic Virus-III (HTLV-III) with an Immunoassay Employing a Recombinant *Escherichia coli*-Derived Viral Antigenic Peptide", Bio/Technology, 3 (10/85) 905-9.

Robert-Guroff et al., "A Monoclonal Antibody Specific for a 52,000-Molecular-Weight Human T-Cell Leukemia Virus-Associated Gycoprotein Expressed by Infected Cells", J. Virology 53 (1/85) 214-220.

Mortimer et al., "Which Anti-HTLV III/LAV Assays for Screening and Conformatory Testing?", Lancet (10/19/85) 873-7.

Crowl et al., "HTLV-III env Gene Products Synthesized in *E. coli* are Recognized by Antibodies Present in the Sera of AIDS Patients", Cell 41 (7/85) 979-86.

Chang et al., "An HTLV-III Peptide Produced by Recombinant DNA is Immunoreactive with Sera from Patients with AIDS", Nature, 315 (5/9/85) 151-4.

Wang et al., "Detection of Antibodies to Human T-Lymphotropic Virus Type III by Using a Synthetic Peptide of Z1 Amino Acid Residues Corresponding to a Highly Antigenic Segment of GP41 Envelope Protein", Proc. Nat'l. Acad. Sci. USA, 83 (8/86) 6159-63.

Barre-Sinoussi et al., Science 220:868 (1983).

Bolivar et al., Gene 2:95 (1977).

Casadaban et al., J. Mol. Biol. 138:179 (1980).

(List continued on next page.)

*Primary Examiner*—Christine M. Nucker

*Attorney, Agent, or Firm*—Jon S. Saxe; George M. Gould; Norman C. Dulak

[57] ABSTRACT

The present disclosure relates to synthetic peptides derived from the conserved region of the HTLVIII envelope proteins. These peptides are useful as reagents for immunoassays for detection of AIDS antibodies, as components of immunogenic compositions useful as vaccines, and for the production of anti-bodies selective to said envelope protein and methods for detecting the presence of AIDS antibodies in biological fluid samples.

20 Claims, 2 Drawing Sheets

OTHER PUBLICATIONS

Kitchen et al., Nature 312:367 (1984).
Lacal et al., Proc. Natl. Acad. Sci. USA 81:5305 (1984).
Lomedico et al., Nature 312:458 (1984).
Montagnier et al., *Human T-Cell Leukemia/Lymphoma Viruses,* Cold Spring Harbor, New York, Conference Date Sep. 14–16, 1983, Published 1984.
Sarngadharan et al., Science 224:506 (1984).
Schupbach et al., Science 224:503 (1984).
Sutcliffe, Nucleic Acids Res. 5:2721 (1978).
Ratner et al., "Complete Nucleotide Sequence of the AIDS Virus, HTLV-III", Nature, vol. 313, pp. 277–284, Jan. 24, 1985.
Sanchez-Pescador, R. et al., "Nucleotide Sequence and Expression of an AIDS-Associated Retrovirus (ARV-2)", Science, vol. 227, pp. 484–492, Feb. 1, 1985.
Wain-Hobson, S. et al., "Nucleotide Sequence of the AIDS Virus, LAV", Cell, vol. 40, pp. 9–17, Jan. 1985.
Kiyokawa, T. et al., "Envelope Proteins of Human T-Cell Leukemia Virus: Expression in *Escherichia coli* and its Application of Studies of Env. Gene Functions", Proc. Natl. Acad. Sci. USA, vol. 81, pp. 6202–6206, Oct. 1984.

FIG. 1A 10 20
Met Arg Val Lys Glu Lys Tyr Gln His Leu Trp Arg Trp Gly Trp Arg Trp Gly Thr Met 30 40
Leu Leu Gly Met Leu Met Ile Cys Ser Ala Thr Glu Lys Leu Trp Val Thr Val Tyr Tyr 50 60
Gly Val Pro Val Trp Lys Glu Ala Thr Thr Thr Leu Phe Cys Ala Ser Asp Ala Lys Ala 70 80
Tyr Asp Thr Glu Val His Asn Val Trp Ala Thr His Ala Gly Val Pro Thr Asp Pro Asn 90 100
Pro Gln Glu Val Val Leu Val Asn Val Thr Glu Asn Phe Asn Met Trp Lys Asn Asp Met 110 120
Val Glu Gln Met His Glu Asp Ile Ile Ser Leu Trp Asp Gln Ser Leu Lys Pro Cys Val 130 140
Lys Leu Thr Pro Leu Cys Val Ser Leu Lys Cys Thr Asp Leu Lys Asn Asp Thr Asn Thr 150 160
Asn Ser Ser Ser Gly Arg Met Ile Met Glu Lys Gly Glu Ile Lys Asn Cys Ser Phe Asn 170 180
Ile Ser Thr Ser Ile Arg Gly Lys Val Gln Lys Glu Tyr Ala Phe Phe Tyr Lys Leu Asp 190 200
Ile Ile Pro Ile Asp Asn Asp Thr Thr Ser Tyr Thr Leu Thr Ser Cys Asn Thr Ser Val 210 220
Ile Thr Gln Ala Cys Pro Lys Val Ser Phe Glu Pro Ile Pro Ile His Tyr Cys Ala Pro 230 240
Ala Gly Phe Ala Ile Leu Lys Cys Asn Asn Lys Thr Phe Asn Gly Thr Gly Pro Cys Thr 250 260
Asn Val Ser Thr Val Gln Cys Thr His Gly Ile Arg Pro Val Val Ser Thr Gln Leu Leu 270 280
Leu Asn Gly Ser Leu Ala Glu Glu Glu Val Val Ile Arg Ser Val Asn Phe Thr Asp Asn 290 300
Ala Lys Thr Ile Ile Val Gln Leu Asn Thr Ser Val Glu Ile Asn Cys Thr Arg Pro Asn 310 320
Asn Asn Thr Arg Lys Lys Ile Arg Ile Gln Arg Gly Pro Gly Arg Ala Phe Val Thr Ile 330 340
Gly Lys Ile Gly Asn Met Arg Gln Ala His Cys Asn Ile Ser Arg Ala Lys Trp Asn Ala 350 360
Thr Leu Lys Gln Ile Ala Ser Lys Leu Arg Glu Gln Phe Gly Asn Asn Lys Thr Ile Ile 370 380
Phe Lys Gln Ser Ser Gly Gly Asp Pro Glu Ile Val Thr His Ser Phe Asn Cys Gly Gly 390 400
Glu Phe Phe Tyr Cys Asn Ser Thr Gln Leu Phe Asn Ser Thr Trp Phe Asn Ser Thr Trp 410 420
Ser Thr Glu Gly Ser Asn Asn Thr Glu Gly Ser Asp Thr Ile Thr Leu Pro Cys Arg Ile 430 440
Lys Gln Phe Ile Asn Met Trp Gln Glu Val Gly Lys Ala Met Tyr Ala Pro Pro Ile Ser

FIG. IB

```
                                    450                                          460
            Gly Gln Ile Arg Cys Ser Ser Asn Ile Thr Gly Leu Leu Leu Thr Arg Asp Gly Gly Asn

                                    470                                          480
            Asn Asn Asn Gly Ser Glu Ile Phe Arg Pro Gly Gly Gly Asp Met Arg Asp Asn Trp Arg

                                    490                                          500
            Ser Glu Leu Tyr Lys Tyr Lys Val Val Lys Ile Glu Pro Leu Gly Val Ala Pro Thr Lys

                                    510                                          520
            Ala Lys Arg Arg Val Val Gln Arg Glu Lys Arg Ala Val Gly Ile Gly Ala Leu Phe Leu

                                    530                                          540
            Gly Phe Leu Gly Ala Ala Gly Ser Thr Met Gly Ala Ala Ser Met Thr Leu Thr Val Gln

                                    550                                          560
            Ala Arg Gln Leu Leu Ser Gly Ile Val Gln Gln Gln Asn Asn Leu Leu Arg Ala Ile Glu

                                    570                                          580
            Ala Gln Gln His Leu Leu Gln Leu Thr Val Trp Gly Ile Lys Gln Leu Gln Ala Arg Ile

                                    590                                          600
            Leu Ala Val Glu Arg Tyr Leu Lys Asp Gln Gln Leu Leu Gly Ile Trp Gly Cys Ser Gly

                                    610                                          620
            Lys Leu Leu Cys Thr Thr Ala Val Pro Trp Asn Ala Ser Trp Ser Asn Lys Ser Leu Glu

                                    630                                          640
            Gln Ile Trp Asn His Thr Thr Trp Met Glu Trp Asp Arg Glu Ile Asn Asn Tyr Thr Ser

                                    650                                          660
            Leu Ile His Ser Leu Ile Glu Glu Ser Gln Asn Gln Gln Glu Lys Asn Glu Gln Glu Leu

                                    670                                          680
            Leu Glu Leu Asp Lys Trp Ala Ser Leu Trp Asn Trp Phe Asn Ile Thr Asn Trp Leu Trp

                                    690                                          700
            Tyr Ile Lys Leu Phe Ile Met Ile Val Gly Gly Leu Val Gly Leu Arg Ile Val Phe Ala

                                    710                                          720
            Val Leu Ser Val Val Asn Arg Val Arg Gln Gly Tyr Ser Pro Leu Ser Phe Gln Thr His

                                    730                                          740
            Leu Pro Ile Pro Arg Gly Pro Asp Arg Pro Glu Gly Ile Glu Glu Glu Gly Gly Glu Arg

                                    750                                          760
            Asp Arg Asp Arg Ser Ile Arg Leu Val Asn Gly Ser Leu Ala Leu Ile Trp Asp Asp Leu

                                    770                                          780
            Arg Ser Leu Cys Leu Phe Ser Tyr His Arg Leu Arg Asp Leu Leu Leu Ile Val Thr Arg

                                    790                                          800
            Ile Val Glu Leu Leu Gly Arg Arg Gly Trp Glu Ala Leu Lys Tyr Trp Trp Asn Leu Leu

                                    810                                          820
            Gln Tyr Trp Ser Gln Glu Leu Lys Asn Ser Ala Val Ser Leu Leu Asn Ala Thr Ala Ile

                                    830                                          840
            Ala Val Ala Glu Gly Thr Asp Arg Val Ile Glu Val Val Gln Glu Ala Tyr Arg Ala Ile

                                    850                        856
            Arg His Ile Pro Arg Arg Ile Arg Gln Gly Leu Glu Arg Ile Leu Leu  .
```

HTLV-III ENVELOPE PEPTIDES

FIELD OF THE INVENTION

This invention relates to synthetic peptides, designated HTLV-III env whose sequence represent a conserved region of the viral envelope protein of the etiologic agent for Acquired Immune Deficiency Syndrome (AIDS), or derivatives of such peptides and the use of such peptides and/or derivatives in methods for detecting the presence of AIDS antibodies in human blood. Additionally, such peptides can be utilized in immunogenic compositions which can be used as vaccines or to elicit antibodies in host animals, which antibodies in turn can be employed to detect the HTLV-III virus in biological fluid specimens.

The results disclosed herein are based in part on the techniques and concepts of the field of immunology. For convenience, certain terms commonly used in the art are defined herein. The term "immunochemical reaction" is used to denote the specific interaction which occurs beteen an antigen and its corresponding antibody, regardless of the method of measurement. Such a reaction is characterized by a non-covalent binding of one or more antibody molecules to one or more antigen molecules. The immunochemical reaction may be detected by a large variety of immunoassays known in the art. The terms "immunogenic" or "antigenic" will be used here to describe the capacity of a given substance to stimulate the production of antibodies specifically immunoreactive to that substance when that substance is administered to a suitable test animal under conditions known to elicit antibody production. The term "protective antigen" refers to the ability of a given immunogen to confer resistance in a suitable host, against a given pathogen. The term "epitope", refers to a specific antibody binding site on an antigen. Macromolecular antigens such as proteins typically have several epitopes with distinctive antibody binding specificities. Different epitopes of the same antigen are distinguishable with the aid of monoclonal antibodies which, due to their high degree of specificity, are directed against singly epitopes. Two different monoclonal antibodies directed against different epitopes on the same antigen may each bind the antigen without interfering with the other, unless the epitopes are so close together that the binding of one sterically inhibits the binding of the other. The term "immunodominant region" denotes an area of the antigen molecule which is mainly responsible for its antigenicity.

BACKGROUND OF THE INVENTION

From 1981 to date, there have been over thirteen thousand (13,000) people diagnosed as having acquired immune deficiency syndrome (AIDS). AIDS has been characterized by the onset of severe opportunistic infections secondary to an effect on the body's immune system. Gottlieb, MS. et al., Pneumocystis Carinic Pneumonia and Mucosal Condidisis in previously healthy homosexual men: evidence of a new acquired cellular immuno-deficiency, N. Eng. J. Med. 305, 1426–1431 (1981). The disease has been found in male homosexuals, patients receiving blood products, intraveneous drug addicts, and individuals originating from Haiti and Central Africa. Piot, P. et al, Acquired immunodeficiency syndrome in a heterosexual population in Zaire. Lancet 11, 65–69 (1984). The causative agent was suspected to be of viral origin as the epidemiological pattern of AIDS was consistent with a transmissible disease. At least three (3) retroviruses have been isolated from cultured T-cells of several patients with AIDS, or from white blood cells of persons at risk for the disease. A novel human retrovirus called lymphadenopathy-associated virus (LAV) was discovered and its properties were consistent with its etiological role in AIDS. That virus was isolated from a patient with lymphadenopathy and hence the name. Montagnier, L. et al. A New Human t-lymphotropic retrovirus: Characterization and possible role in lymphadenopathy and acquired immune deficiency syndromes. In Human T-Cell Leukemia/Lymphoma Virus, R. C. Gallo, M. Essex and L. Gross, eds. (Cold spring Harbor, N.Y.: Cold Spring Harbor Laboratory) pp. 363–370. Other human retroviruses, specifically two subgroups of the human t-cell leukemia/lymphoma/lymphotropic virus, types I and III have been isloated. (HTLV-I: Poicsz, B. J. et al. PNAS (USA) 77, 7415 (1980)); (HTLV-III: Popovic, M. et al. Detection, isolation and continuous production of cytopathic retroviruses (HTLV-III) from patients with AIDS and pre-AIDS. Science 224, 797–500 (1984)). Still another virus, the AIDS associated retrovirus (ARV), was proposed as the causative agent. Levy, J. A. et al. Isolation of lymphocytopathic retroviruses from San Francisco patients with AIDS. Science 225, 840–842 (1984)). Both the HTLV-III and ARV retroviruses display biological and sero-eidemiological properties similar to LAV. Levy et al., supra, Popovic et al. supra. As seen from the above, at least three (3) retroviruses have been postulated as the etiologic agent or AIDS: LAV; ARV; and, HTLV subtypes I and III.

LAV, HTLV-III and ARV-II genomes have been molecularly cloned. Shaw, G. M. et al., Serological analysis of a subgroup of human T-lymphotropic retroviruses (HTLV-III) associated with AIDS. Science 224, 503–505 (1984). Alizon, M. et al. Molecular Cloning of lymphadenopathy - associated virus. Nature, in press. The complete nucleotide sequence of the proviral genome of LAV, ARV and HTLV-III has been determined. Ratner, L. et al. Complete nucleotide sequence of the AIDS virus, HTLV-III. Nature 313, 277–284 (1985); Sanchez-Pescadov, R. et al. Nucleotide sequence and expression of an AIDS-associated retrovirus (ARV-2). Science 227, 484–492 (1985); and, Wain-Hobson, S. et al. Nucleotide sequence of the AIDS virus, LAV. Cell 40, 9-17 (1985).

One reason for the difficulty in determining the etiologic agent of AIDS was due to the reactivity of various retroviral antigens with serum samples from AIDS patients. For example, serum samples from AIDS patients have been shown to react with antigens of HTLV-I and HTLV-III. (HTLV-I: Essex, M., et al., "Antibodies to Cell Membrane Antigens Associated with Human T-Cell Leukemia Virus in Patients with AIDS", Science 220, 859(1983)); (HTLV-III: Sarngadharan, M. G. et al., "Antibodies Reactive With Human T-Lymphotropic Retroviruses (HTLV-III) in the Serum of Patients With AIDS", Science 224, 506–508 (1984)). Envelope gene products of HTLV demonstrated antigenicities cross-reactive with antibodies in sera from adult T-cell leukemia patients. Kiyokana, T. et al. Envelope proteins of human T-cell leukemia virus: Expression in *Escherichia coli* and its application to studies of env gene "functions" PNAS (USA) 81, 6202–6206 (1984). Adult T-cell leukemias (ATL) differ from acquired immune deficiency syndrome (AIDS) in that HTLV-I causes T-cell malignancies, that is uncontrolled growth of T-cell. In AIDS rather than cell growth there is cell death. In fact this cytopathic characteristic of HTLV-III was critical to determining ultimately the specific retroviral origin of the disease. Thus the etiologic agent of AIDS was isolated by use of immortalized human neoplastic T cell lines (HT) infected with the cytopathic retrovirus characteristic of AIDS, isolated from AIDS afflicted patients. Seroepidemiological assays using this virus showed a complete correlation between AIDS and the presence of antibodies to HTLV-III antigens. Gallo et al. supra 1984; Sarngadharan et al. supra 1984; Schupbach et al. Serological Analysis of a subgroup of human T-lymphotropic retroviruses (HTLV-III) associated with AIDS, Science 224, 503–505 (1984). In addition, nearly 85% of patients with lymphadenopathy syndrome and a significant proportion of asymptomatic homosexual men in AIDS endemic areas were also found to carry circulating antibodies to HTLV-III. Taken together, all these data indicate HTLV-III to be the etiologic agent for AIDS.

Until the successful culturing of AIDS virus using H-9 cell line the env AIDS protein of the AIDS virus had not been isolated, characterized or synthesized. This, in a major part, is due to the fact that the virus is cytopathic and thus isolation of the virus was not possible. Popovic M. et al., Detection, Isolation, and Continuous Production of Cytopathic Retroviruses (HTLV-III) From Patients With AIDS and Pre AIDs, Science 224, 497–500 (1984). Once the human T-cell line resistant to the cytopathic effects of the virus was discovered, a molecular clone of proviral DNA could be achieved.

The need for a sensitive and rapid method for the diagnosis of AIDS in human blood and its prevention by vaccination is very great. Virtually all the assays/tests presently available are fraught with errors. In fact the Center for Disease Control (CDC) has indicated that presently available tests be used solely for screening units of blood for antibody to HTLV-III. The CDC went further by stating that the presently available ELISA tests not be used for general screening of high risk populations or as a diagnostic test for AIDS. Federal Register 50(48), 9909, March 12, 1985. The errors have been traced to the failure to use a specific antigenic protein of the etiologic agent for AIDS. The previously used proteins were derived from a viral lysate. Since the lysate is made from human cells infected with the virus, i.e. the cells used to grow the virus, the lysate will contain human proteins as well as viral proteins. Thus preparation of a pure antigen of viral protein is very difficult. The antigen used produced both false positive and false negative results. Budiansky, S., AIDS Screening, False Test Results Raise Doubts, Nature 313, 583(1984).

The errors caused by the use of such lysate proteins/-peptides can be avoided by using a composition for binding AIDS antibodies which is substantially free of the non-AIDS specific proteins. Compositions that are substantially pure HTLV-III env peptide fragments of the present invention can be used as antigens. The HTLV-III env peptides of the instant invention encompass a highly conserved epitope sequence designated HTLV-III env (500–511) which permit their use to screen for, diagnose and/or prevent by vaccination of the AIDS virus.

A synthetic peptide representing HTLV-III env (477–491) and its use as an immunogen for production of monoclonal antibodies which specifically bind to the envelope region of HTLV-III and which are used in a diagnostic reagent in an enzyme linked immunosorbent assay are described in U.S. Patent Application Ser. No. 779,431, filed Sept. 24, 1985, title HTLV-III/LAV Synthetic Peptide, Inventors F. Wong-Staal et al.

BRIEF DESCRIPTION OF THE FIGURE

This invention may be more readily understood by reference to FIG. 1, in which FIG. 1A shows the first 440 residues of the amino acid sequence of the complete env protein of HTLV-III beginning at the amino-terminus, and FIG. 1B shows the remaining residues of the protein.

DESCRIPTION OF THE INVENTION

The peptides of the present invention can be represented by the following formula:

W-X-Lys-Ala-Lys-Arg-Arg-Val-Val-Gln-Arg-Glu-Lys-Arg-Y-Z where W is H-, Cys- or Tyr-, X is a bond or a sub-sequence of one or more amino acids starting from the carboxyl terminus of HLTV-III env (460–499), Y is a bond or a sub-sequence of one or more amino acids starting from the amino terminus of HTLV-III env (512–550), and Z is -OH, -$NH_2$ -Cys-$NH_2$, provided however that one of X or Y is a bond.

As disclosed herein, amino acids are numbered as described in FIG. 1.

The derivatives of the peptide of formula I having cysteine at either the amino or the carboxy terminus are utilized to provide improved coupling of the peptide to immunogenic carrier materials when the peptide is to be utilized as an immunogen to elicit antibody formation. The derivatives of formula I, wherein W is tyrosine, provide a preferred substrate for radio-iodination thereby allowing such compounds to be utilized as radio-labelled ligands in a radioimmunoassay for HTLV-III antibody in test fluids.

A preferred aspect of the compounds of the present invention is obtained by compounds of formula I wherein X is a sub-sequence of one or more amino acids starting from the carboxyl terminus of HLTV-III env (460–499) and Y is a bond. A preferred embodiment of this aspect if the invention is obtained when said sub-sequence consists of HLTV-III Env (487–499). Thus particularly preferred species of this embodiment consist of HLTV-III env (487–511) Cys-$NH_2$ and HTLV-III env Tyr (487–511) Cys-$NH_2$.

In another preferred aspect of the compounds of the present invention compounds of formula I wherein both X and Y are bonds are provided. Preferred embodiments of this aspect of the invention include HTLV-III env (500–511) Cys-$NH_2$, HTLV-III env Cys-(500–511) $NH_2$ and HTLV-III env Tyr (500–511) $NH_2$.

Compounds of the present invention of formula I can be conveniently prepared by utilizing conventional solid phase peptide synthesis methods well-known in the art. In such synthetic method, a polymeric solid-phase support to which the amino acids used in the synthesis are covalently anchored in sequence starting from the carboxyl terminus is used. Automated solid-phase peptide synthesizers suitable for carrying out such methodology are commercially available and synthesis is carried out according to the instructions of the manufacturer. In the event an amide group is desired at the carboxyl terminus for compounds of formula I, then the resin employed is a benzylhydrylamine resin which is an article of commerce. Cleavage of the peptide chain from such resin results in the formation of an amide group as desired at the carboxyl terminus.

Upon completion of the automated peptide synthesis, the desired peptides are removed from the resin utilizing methods well-known in the art, e.g. anhydrous liquid HF. This treatment also cleaves off any side chain protecting groups. The product peptide can then be purified in conventional manner, such as, for example, by utilizing high performance liquid chromatography preferably with a reverse phase $C_{18}$ type column.

DETAILED DESCRIPTION OF THE INVENTION

In accordance with the present invention, the search for the env protein of the etiologic agent for Acquired Immune Deficiency Syndrome (AIDS) has lead to the isolation and sequencing and expressing of the proviral gene of the AIDS virus. It has now been discovered, that the postulated etiologic agents of AIDS, lymphadenophathy-associated virus (LAV), AIDS-associated - retrovirus (ARV) and human T-cell leukemia/lympha/lymphotropic virus, HTLV-III, are in fact variants of the same virus. For purposes of this invention and claims, the virus causing AIDS will be referred to herein as AIDS virus. AIDS virus will be understood to include the variants which have been postulated as the causative agent of AIDS, namely, LAV, ARV and HTLV-III. The env protein of the AIDS virus (env AIDS) is a 97,200 dalton protein with 32 potential N-glycosylation sites. Nucleotide sequence analysis of the AIDS env. gene of the putative etiologic agents of AIDS demonstrates that all the viruses are variants of the same virus. There has been found to be approximately 1 to 20% divergents of variation from the sequence from the env. gene of HTLV-III and the sequences of the env genes of the other viruses LAV and ARV-II.

The integrated proviral genome of HTLV-III was cloned from the genomic DNA of H9 cells infected with HTLV-III. See Shaw et al., Science 226, 1165–1171 (1984). The comparative nucleotide sequences of LAV, ARV-II and HTLV-III have been determined by Ratner, Nature 313, 277–284 (1985); Sanchez-Pescadov et al., Science 227, 484–492 (1985); and Wain-Hobson et al., Cell 40, 9–17 (1985) respectively.

One of the conserved regions in these various viral env. gene sequences is the region corresponding to amino acids 460–550 which contains the important epitopic site around 500–511. It is thus believed that such region provides a preferred antigenic site for use in detection of the presence of AIDs viruses or antibodies directed thereto present in the sera of human subjects. Of particular importance to note is the processing sites located within amino acids 500–511 which undergo proteolytic cleavage in the viral envelope. The resulting two peptides have portions of the general conserved regions embodied in amino acids 460–550 at their carboxyl and amino termim respectively thus allowing antibody specific to this epitopic area raised from the peptides of the invention to recognize both processed proteins. Moreover, peptides constructed with such sequences would have superior chances to provide vaccines which could immunize populations against all three of AIDs viral entities.

In one diagnostic embodiment of the present invention, the peptides of formula I can be employed in a sandwich type enzyme immunoassay to directly detect the presence of antibody to AIDS virus in serum samples. Such assay can be carried out quite simply by coating microtiter plates with a dilute solution of a peptide of formula I, preferably where W is H and Z is $-NH_2$ or Cys-$NH_2$. The peptide coated microtiter plates can then be incubated with the test sample for sufficient time to allow any antibody present to complex with the peptide. After the incubation period has been completed, the serum sample is removed, the plates are washed and then treated with anti-human IgG coupled to an enzyme such as horseradish peroxidase. Such reagents are articles of commerce. If any antibody to AIDS virus is present in the serum sample, it will be bound by the peptide and will be complexed to the anti-human IgG bearing the enzyme label. After removal of the reagent, substrate for the enzyme is added and allowed to incubate in the microtiter plate. If antibody were present in the sample, a color reaction will be observed in the microtiter plate.

In an alternative diagnostic embodiment, compounds of formula I wherein W is tyrosine are radioiodinated in a conventional manner such as, for example, by use of chloramine-T utilizing $^{125}I$ as the radioactive ligand. Antibodies specific for AIDS virus can be obtained by utilizing compounds of formula I where either W or Z is cysteine as haptens in the preparation of an immunogenic composition. Such immunogenic composition is prepared by bonding the aforesaid haptens through the indicated cysteine moiety to a conventional immunogenic carrier material. As used herein, the term "immunogenic carrier material" is meant to include those materials which have the property of independently eliciting an immunogenic response in a host animal and which can be covalently coupled to the above described haptens preferably through said cysteine moiety. Suitable carrier materials include, for example, proteins; natural or synthetic polymeric compounds, such as, polypeptides, e.g., polylysine or copolymers of amino acids, polysaccharides; and the like. Particularly preferred carrier materials are proteins and polypeptides, especially proteins.

The identity of the protein material utilized in the preparation of an immunogen useful in the instant invention is not critical. Examples of suitable proteins useful in the practice of this invention include mammalian serum proteins such as, for example, human gamma globulin, human serum albumin, bovine serum albumin, methylated bovine serum albumin, rabbit serum albumin and bovine gamma globulin. A particularly preferred protein for this purpose is keyhole limpet hemocyanin.

The covalent coupling of the peptide hapten to the immunogenic carrier material can be carried out in the manner well-known in the art. Reagents suitable for this purpose include N-succinimide esters, carbodiimides, EEDQ(N-ethoxycarbonyl-2-ethoxy-1,2-dihydroquinoline) and the like. A particular preferred reagent for use in coupling the peptide hapten to the keyhole limpet hemocyanin of the preferred embodiment is m-maleimido- benzoyl-N-succinimide ester.

The aforesaid immunogen may be utilized to induce formation of antibodies specific to AIDS virus in host animals by injecting the immunogen in such a host preferably using an adjuvant known in the art such as complete or incomplete Freund's adjuvant. Improved titers can be obtained by repeated injections over a period of time. Suitable host animals for this purpose include mammals such as, rabbits, horses, goats, guinea pigs, rats, cows, sheep, etc. The resulting antiserum will contain antibodies which will selectively complex with AIDS virus, e.g. HTLV-III preparations containing the env (460–550) epitope. The anti-serum can be affinity purified in a manner known per se by passing such anti-serum over an affinity column prepared from a peptide of formula I, preferably where W is Cys, coupled to a solid support matrix such as Sepharose.

In a further aspect of this invention it is possible to produce monoclonal antibodies specific to the aforesaid 460–550 epitope of the env gene of HTLV-III. The production of monoclonal antibodies can be carried out according to the general procedure described by Kohler and Milstein, Nature 256, 495–597 (1975). The resulting hybrid cells produced by this method have the property of secreting an antibody of predefined specificity. This specificity is that of the antibody produced by lymphocytes involved in the fusion. The hybrid cells may be cloned and grown in stable culture to produce in the culture supernatant samples of antibody to a specific determinant or epitope.

The general method of production of hybrid cell lines of the type described above comprises the steps of immunizing an animal (usually a rat or mouse but not necessarily one of those) with the described immunogen, i.e. a peptide of formula I wherein W or Z is cysteine covalently bonded to an immunogenic carrier material. After allowing time for the immune system to generate lymphocytes secreting the antibody to the immunogen, the animal is sacrificed and a suspension of the spleen is prepared. Fusion between these cells and myeloma cells is achieved by bringing them into contact in the presence of a fusion promoter (e.g. polyethylene glycol). A small percentage of the cells fuse to produce hybrid myeloma cells. The immunization results in a plurality of different lymphocytes each secreting antibody to a different antigenic determinant, and these characteristics are transferred genetically to the hybrid cells. It is possible, by careful screening, to isolate from a culture of hybrid cells, a cell having the desired specificity to the 460–550 epitope of the env region of the HTLV-III virus. Such cells may be cloned and cultured by methods now well-known in the art so as to provide a continuous source of the desired monoclonal antibody.

Any conventional immuno assay method now known in the art may be employed using the antibodies of the invention. For example, a suitable radioimmunoassay method utilizing the above described reagents can be carried out by mixing a sample containing the HTLV-III virus with a known amount of the labelled tyrosine analog of formula I and the HTLV-III (460–550) env protein specific monoclonal or polyclonal antibody, measuring the degree of binding of the labelled analog and determining the amount of AIDS virus present in said sample by comparing said degree of binding to a standard curve obtained by mixing known amounts of AIDS virus with fixed amounts of said labelled analog and said antibody and determining the degree of binding for each known amount of virus or viral protein.

Another diagnostic embodiment of the invention provides a radioimmune assay for detecting the presence of AIDs antibodies in sera. In such assay sera samples are serially diluted in buffer and mixed with a radio iodinated analog of a peptide of formula I where W is Tyr. After incubation, anti-human IgG is added and the mixture incubated again. After centrifugation, the radioactivity bound to the precipitated antibody complex is measured. The presence of AIDs antibody is detected by count values in excess of those observed as background for normal patient sera.

In a further diagnostic aspect of the invention, an immunometric assay procedure may be run utilizing the antibodies of the present invention produced above. In a representative embodiment of such assay method duplicate samples are run. The procedure employs 100 μl of a suspension of antibody immobilized on Agarose particles mixed with 100 μl of serum and 100 μl of soluble 125I-labelled antibody. This mixture is allowed to incubate for a time period ranging from ¼ hour to 24 hours. Following the incubation, the Agarose particles are washed by addition of buffer and then centrifuged. After removal of the washing liquid by aspiration, the resulting pellet of Agarose particles is then counted for bound 125I-labeled antibody. The counts obtained for each of the complexes can then be compared to controls.

In a further aspect of the present invention, the peptides of formula I particularly those having W or Z as cysteine can be incorporated into vaccines capable of inducing protective immunity against the AIDS virus. Known techniques may be employed for enhancing the antigenicity of such peptide vaccine preparations, for example, by coupling such peptide through the cysteine moiety to a toxoid such as diptheria toxoid or tetanus toxoid. It is also possible to couple such peptides to inorganic carrier materials which enhance immunogenicity by presenting such peptides to the host subject in the manner approximating the normal antigen on the viral surface. Such inorganic carrier materials include aluminum hydroxide. It is within the skill of the art to use such vaccine composition in combination with adjuvants or other enhancers of immune response, such as, immune interferon interleukin-2, thymosin alpha 1 and the like. In addition, the vaccine composition may comprise other anitgens to provide immunity against other diseases in addition to AIDS, such as, for example, hepatitis core or surface antigens. It is also within the skill of the art to produce a vaccine composition incorporating the peptides of the present invention into lipsomes as a means of maintaining the peptides in a desirable orientation for inducing immunity in a host.

Routes of administration, antigen dose, number and frequency of injections are all matters of optimization within the scope of ordinary skill in the art, particularly in view of the fact that there is experience in the art in providing protective immunity by injection of other related antigens to provide immunity in other viral infections. It is anticipated that the principal value of providing immunity to AIDS infection will be for those individuals who have had no previous exposure to AIDS, e.g., individuals who are in the high risk population, such as, homosexuals, drug addicts, Hatians and Central Americans, and individuals who may be receiving blood transfusions. It is also anticipated that temporary immunity for infants may be provided by immunization of mothers during pregnancy.

Because anti-HTLV-III antibodies are found in more than 90% of the AIDS patients, it was of interest to see if the synthetically produced peptides of the present invention are immunoreactive with these antibodies.

For this analysis purified peptide of formula I wherein W is H and Z is Cys-$NH_2$ was transferred to a nitrocellulose filter by using Western blotting technique. Strips of the filter containing transferred peptide were reacted with 1,000-fold diluted human sera and the antigen-antibody complex formed as detected by incubation of the strips with $^{125}$I-labelled *Staphylococus aureus* protein A followed by autoradiography. Bands corresponding to the peptide were consistently observed when the serum used was from patients with AIDS syndrome. The negative controls used were normal human sera and serum from a patient with HTLV-I infection. No reaction was observed with sera from healthy individuals or from HTLV-I infected individuals. Patient sera was derived from all parts of the United States including California and all AIDS patients sera tested, so far, were found to be positive. These results indicate that the epitopic region corresponding to positions 460-550 of the envelope protein are recognized by antibodies found in AIDS patients.

In further experiments it was found that polyclonal antibodies elicited from the same peptides coupled to keyhole limpet hemocyanin elicited in rabbits will immunoblot with recombinant HTLV-III env protein.

The above results indicate that peptides of formula I, as described above, will be suitable for use in the diagnostic assays and vaccine compositions described.

The present invention is further illustrated by the following examples. In such examples the abbreviation Tos means tosylate, 2-ClZ means 2-chlorocarbobenzoxy, OBzl means 0-benzyl and Dmb means dimethylbenzyl. Boc means benzoxycarbonyl, Dcb is 2,6-dichlorobenzyl.

EXAMPLE 1

Preparation of Boc-Cys(Dmb)-Benzhydrylamine-resin 1

Benzhydrylamine-resin (BHA) (20 g, 0.5-0.7 meg/g) was coupled with Boc-Cys(Dmb)-OH (13.24g, 40.7mmol) in $CH_2Cl_2$ (250 mL) with dicyclohexyl carbodiimide (DCC) (8g,) for 4 hours. The resultant Boc-Cys(Dmb)-BHA- resin was washed with $CH_2Cl_2$ (3×300mL), DMF (2×300mL), MeOH (3×300mL), $CH_2Cl_2$ (3×300mL) and dried. An aliquot was hydrolyzed (1mL of 6M propionic HCl at 130° for 2 hours). Amino acid analysis showed a substitution of 0.52 mmol of Cys per gram of resin. The remaining amino groups were acetylated with $AC_20$-pyridine - yield: 28.75g

EXAMPLE 2

Preparation of HTLV-III env (500–511)-Cys-$NH_2$, 2

Boc-Cys(Dmb)-BHA-resin (2.0g, 1.0mmol) from Example 1 was charged into the reaction vessel of the Vega 250 Peptide Synthesizer and solid phase synthesis was performed by the symmetric anhydride procedure for a total of 12 cycles with the following $N^{\alpha}$- Boc amino acids:

Arg(Tos), Lys(2-ClZ), Glu(OBzl), Arg(Tos), Gln, Val, Val, Arg(Tos), Arg(Tos), Lys(2-ClZ), Ala and Lys(2-ClZ)

to give 3.9g of protected peptide resin. The protected peptide resin (1.5g) was treated with anhydrous liquid HF containing 10% dithioethane of 0° for 1 hour. The HF was evaporated at 0° (high- vac, CaO trap) and the crude peptide and resin mixture triturated with EtOAC, - extracted with TFA, evaporated and the residue triturated with ether and dried. Yield: 700mg. A part of the crude material (350mg) was dissolved in 10ml of $H_20$ (containing 0.5% TFA), filtered (0.45μ type HA Millipore filter) and loaded onto a Nucleosil C 18 (5μ ) column (1×50 cm).

The column was eluted (2mL/min.) with a solvent system consisting of (A) $H_20$ (containing 0.1% TFA) and (B) $CH_3CN$ (containing 0.1% TFA) in a linear gradient mode: 5–25% (B) in 180 minutes with a flow rate of 2mL/min. Fractions were collected (2 minutes/-fraction) and aliquot analyzed by the analytical hplc system. The product emerged in fractions 54–55 which were combined, evaporated and lyophilized to give pure HTLV-III env (500–511)-Cys-$NH_2$. Yield: 8.5mg. The product was shown to be homogeneous by analytical hplc and gave the expected amino acid composition (6N HCl, 1% TGA; 110°; 72 hours): Glu 2.04; Ala, 1.00; Val,* 1.10; Lys, 2.94; Arg. 3.98. Sequence analysis confirmed the amino acid sequence to be HTLV III env (500–511)-Cys-$NH_2$.

*Low value due to difficult Val-Val cleavage.

EXAMPLE 3

Conjugation of HTLV-III env. (500–511)-Cys-$NH_2$ with Keyhole Limpet Hemocyanin, 3

Keyhole limpet hemocyanin, (Calbiochem, 4mg in 50% glycerol) was added to a solution of m-maleimidobenzoyl-N-succinimide ester (0.7mg) in DMF (0.1mL) at 25° and stirred (magnetically) for 30 minutes. The reaction mixture was charged onto a Sephadex G-25 column (1.2×25 cm) which was previously equilibrated with 0.05M $NaH_2PO_4$ (pH 6.0). Fractions (1mL/min.) were collected and the first major peak (280 nm detection) was pooled {MB-KLH complex}. The HTLV-III env (500–511)-Cys-$NH_2$ peptide (5.0mg. 3.0 mmol) in 1mL of 0.05M $NaH_2PO_4$ (pH 6.0) was added to the solution containing the MB-KLH complex. The pH was adjusted to 7–7.5 by addition of 1.0N NaOH (? 1 amounts) and stirring proceeded at 25° for 3 hours. The reaction mixture was dialyzed (MW cut-off 3500) against Dulbecco's phosphate buffered saline, with repeated changes at 4? over a 60 hour period. The dialyzed solution (8.9mL) was used directly for antibody generation.

EXAMPLE 4

Preparation of Boc-Arg(Tos)-Benzhydrylamine-resin, 4

Benzhydrylamine-resin (40.44g 0.5 mmol/g, 20.22 mmol) was coupled with Boc Arg (Tos)-OH(34.6g, 80.7 mmol) in 25% DMF-$CH_2Cl_2$ with DCC (16.78g, 81.4 mmol) for 2h followed by the addition of 1% diisopropylethylamine and reacted for 0.5 h longer. The resultant Boc-Arg (Tos)-BHA-resin was washed with $CH_2Cl_2$ (3×250 mL), MeOH(3×250 mL), $CH_2Cl_2$ (3×250 mL) and dried. The couplings and washing procedures were repeated and an aliquot was hydrolyzed (1 mL of 6M propionic acid/HCl at 130° for 2 h). Amino acid analysis showed a substitution of 0.35 mmol of Arg per gram of resin. The remaining amino groups were acetylated with $AC_20$-Pyridine. Yield 48.88g (Boc-Arg(Tos)-BHA-resin, 4).

EXAMPLE 5

Preparation of HTLV-III env Cys-(500–511)-BHA-resin, 5

Boc-Arg(Tos)-BHA-resin, 4, (2.0g, 0.7 mmol) was charged into the reaction vessel of the Vega 250 Peptide Synthesizer and 12 cycles of solid phase synthesis performed as in Example 2. At the end of the synthesis the BOC-group of the N-terminal amino acid residue was removed (TFA) and dried to give 2.8g of protected HTLV-III env Cys-(500–511)-BHA-resin, 5.

EXAMPLE 6

Preparation of HTLV-III env Cys-(500–511)-$NH_2$, 6

A 1.5g portion of protected peptide resin 5, was treated with anhydrous liquid HF as in Example 2 yield: 741 mg. A portion of this material (350 mg) was loaded onto a Nucleosil C-18 (5μ), 1×50 cm (dual columns) and the columns eluted (2 mL/min) with a solvent system consisting of (A) $H_20$ (0.1% TFA)-(B) $CH_3CN$(0.1% TFA) in a linear gradient mode: 5% B–25% B in 180 min. Fractions were collected (2 min/-fraction) and the aliquots analyzed by the analytical hplc system. The product emerged in fraction 48 which was evaporated and lyophilized. Yield: 46.1 mg (13%). The product was shown to be homogeneous by analytical hplc and gave the expected amino acid composition (6NHCl-1% TGA; 110?; 72h): Glu, 2.00; Ala, 1.04; Val; 1.36*; Lys, 2.97; Arg 3.98.

*Low value due to the expected incomplete Val-Val cleavage.

EXAMPLE 7

Preparation of HTLV-III env. Tyr (500–511)-$NH_2$, 7

Boc-Arg(Tos)-BHA-resin, (2.0g, 0.7 mmol) was subjected to 12 cycles of peptide synthesis as in Example 2 to give 2.5g of protected HTLV-III env Tyr (500–511)-BHA-resin. A portion of this material (1.5g) was cleaved with HF (as in Example 2) yielding 781 mg of crude peptide which was purified by hplc as in Example 6. The product emerged in fractions 66–68 which were pooled, evaporated and lyophilized. Yield: 42-5 mg (12%). The product was shown to be homogeneous by analytical hplc and gave the expected amino acid composition (6NHCl-1% TGA; 110°; 24h); Glu, 2.10; Ala, 1.04; Val, *0.90; Tyr, 0.86; Lys, 2.89; Arg, 4.10.

*Low value due to the expected incomplete Val-Val cleavage.

EXAMPLE 8

Preparation of of HTLV-III env (487–511)cys-BHA-resin, 8

A 2.2g portion of protected HTLV-III env (500–511)-Cys-BHA-resin from Example 2, was subjected to 13 cycles of solid phase peptide synthesis, treated with TFA and dried to yield 1.8g of side chain protected HTLV-III env (487–511)-BHA-resin 8.

EXAMPLE 9

Preparation of HTLV-III env (487–511)-Cys-$NH_2$, 9

A 1.0 g portion of 8 was treated with anhydrous liquid HF, as in example 2, yield: 435 mg. The crude product was loaded into dual (in series) Synchropals columns (RP-8, 1×25 cm). The columns were eluted (2ml min) with a solvent system consisting of (A) $H_20$ (0.025% TFA) - (B) $CH_3CN$(0.025%TFA) in a linear gradient mode: 5% B–25% B in 120 min. Fractions were collected (2 min/fraction) and aliquots analyzed by the analytical hplc system. The product emerged in fractions 77–82 which were combined, evaporated and lyophilized. Yield 31.1 mg (12%). The product was shown to be homogeneous by analytical hplc and sequence analysis confirmed the amino acid sequence to be HTLV env (487–511)-Cys-$NH_2$.

EXAMPLE 10

Conjugation of HTLV-III env (487–511)-Cys $NH_2$ with Keyhole Limpet Hemocyanin, 10

Conjugation of 5 mg of 9 to keyhole limpet hemocyanin-MB complex (4 mg) was carried out exactly as in Example 3. The final dialyzed solution, 8 mL, was used directly for antibody generation and for detection of HTLV-III env protein antibodies.

EXAMPLE 11 Synthesis of HTLV-III env Tyr-(487–511)-Cys-$NH_2$, 11

An 0.5g portion of side chain protected HTLV-III env (487–511)-Cys-BHA-resin, 8, was subjected to 1 cycle of solid phase peptide synthesis using Boc-Tyr(Dcb), treated with HF as in example 2 and purified by HpLC (as in Example 9. Yield: 15 mg. The product, 11, was homogeneous by analytical hplc.

EXAMPLE 12

ELISA (Enzyme-linked immunosorbance assay)

Human sera and rabbit sera were screened for anti-peptide antibodies by an ELISA assay. Peptides of Examples 2, 6 and 9 were dissolved in bicarbonate-carbonate saline solution (0.05 M bicarbonate-carbonate, pH 9.6; 0.15 NaCl) to give a concentration of 1 μ g/ml. 100 microliters of this solution was pipeted into each microtiter well and the plates dried overnight at 37° C. Each well was then washed three times with PBS/tween buffer (0.02 M sodium phosphate buffer, pH 6.5; 0.15 M NaCl: 0.05% tween-20). The empty microtiter wells were then filled with blocking buffer (10% calf serum; 1% BSA; 0.3% gelatin; 0.5 M NaCl; 20 mM sodium phosphate, pH 7.5; 0.02% sodium azide) to block unreacted sites. After incubation for 1 hr at 37° C, the plates were washed with PBS/Tween buffer and 100 microtiters of various dilutions (100 to 10,000) of test sera were added to the wells. Following incubation at room temperature for 2 hr, the plates were washed with PBS/Tween buffer. Color reactions were then performed by incubating each well with 100 μl of a 1 to 2000 diluted goat anti-human antibody conjugated with horse radish peroxidase. Incubations were carried out for 1 hr, the plates washed with PBS/Tween buffer and 100 μl of substrate solution added. The substrate solution was prepared by dissolving o-phenylene diamine dihydrochloride in 0.1 M citrate buffer of pH 4.5 at a concentration of 400 μg/ml and 4 μl of hydrogen perioxide added to 10 ml of this solution. Color was allowed to develop for approximately 30 min at 37° C. The reaction was stopped by the addition of 50 μl of 2.5 M $H_2SO_4$ and 50 mM $Na_2S_2O_5$ per well and absorption read at 488 nm on a microplate reader.

EXAMPLE 13

Radioimmune Assay

For the radioimmune assay, the amino terminus tyrosine peptides of Examples 7 and 11 were labelled with $^{125}I$ using chloramine T as a catalyst (Greenwood et al., Biochemical Journal, vol. 89, pp. 114–123, 1963). For this procedure, approximately 100 ng of the peptide was dissolved in 50 μl of 0.01 M Tris-HCl buffer, pH 7.5, containing 10 mM NaCl. 1 mC of radioactive iodine ($^{125}I$) was added to the solution followed by 10 μl of Chloramine T solution (2.5 mg/ml). The reaction was carried out for 1 min and the reaction stopped by the addition of 25 μl of sodium meta bisulfite (2.5 mg/ml) solution. The free $^{125}I$ was then removed by column chromatography on a Biogel P-10 column.

For the radioimmune assay, the AIDS patient sera are diluted serially in Buffer I (10 mM tris-HCl buffer pH 7.8 containing 2% BSA, 0.5 mg/ml of NaCl, 1% EDTA and 0.5% Triton X100). 100 μl of each dilution was pipeted into a test tube and mixed with 10,000 cpm of $^{125}I$-labelled peptide. The mixture was incubated for 3 hr at 37° C. 50 μl of goat anti-human antibody was then added to the reaction mixture followed by 1 ml of rinse buffer (0.01 M Tris-HCl buffer pH 7.8, 0.1% Triton X100, 0.1 M NaCl and 1 mM EDTA). The mixture was then incubated for 1 hr at 37° C. and for 2 hr at 4° C. The tubes were then centrifuged at 2500 RPM and the supernatant discarded. The radioactivity bound to the human antibody was measured in a gamma counter. Counts in excess of the levels provided by normal sera indicated the presence of AIDS antibody in the test sera.

EXAMPLE 14

Preparation of Rabbit Antisera Specific for the HTLV-III Peptides

For the producton of rabbit antibodies, the peptide conjugated to KLH was mixed with complete Freunds adjuvant or incomplete Freunds adjuvant in 1:1 proportion. On day 1, 200 μg of the conjugated peptide in complete Freunds adjuvant was injected into the rabbits intradermally on the back at multiple sites. On day 28, 200 μg of the peptide-KLH conjugate in incomplete Freunds adjuvant was injected intradermally on the back at multiple sites. On day 42, a 40 ml test bleed was taken and the antibody titer determined by ELISA assay. The rabbits were boosted again on day 56, with peptide-KLH conjugate in incomplete Freunds adjuvant followed by exsaugination at day 70.

EXAMPLE 15

Affinity Purification of Anti-Peptide Antiserum to Peptide env 500–511

1. 14 ml of rabbit serum was chromatographed on a column of protein A-Sepharose (0.7 cm×20 cm) followed by elution with 0.1 M citrate, pH 3.5. The acid eluate was neutralized and dialyzed vs. PBS. The yield of IgG was 88 mg as determined by absorbance at 280 nm. This is a typical value. The purity of the IgG preparation was determined by immunoelectrophoresis. Essentially all the IgG was removed from the serum by the protein A column. This IgG was obtained in pure form in the acid eluate.
2. An affinity column was constructed using HTLV-III env Cys-(500–511)-$NH_2$. 8 mg of peptide was reacted with 0.4ml of epoxy-Sepharose followed by blocking with ethanolamine. The final coupling yield was 4.2 mg peptide/0.4 ml Sepharose as determined by amino acid analysis. This is about 35% of the theoretical maximum for this resin.
3. 70 mg of the IgG (80% of the sample) was chromatographed on the peptide-Sepharose column followed by elution with 0.2 m glycine, pH 2.5 and neutralization of the acid eluate. The serum was run over the column a second time and the combined acid eluates were dialyzed vs. PBS. The total yield of affinity purified IgG was 1.8 mg (2.5%). This is a reasonably good yield of specific anti-peptide antibody.
4. The extent to which the affinity purification procedure enriched the anti-peptide activity was assessed by ELISA. The criteria which were applied were the retention of anti-peptide reactivity together with the depletion of anti-KLH reactivity. The results showed that the reactivity of the affinity purified IgG toward synthetic peptide compares favorably with that of total IgG and serum. The results also show that the reactivity of the affinity purified IgG toward KLH has dropped to undetectable levels. The anti-KLH activity is all found in the peptide-column breakthrough.
5. To test whether the affinity-purified rabbit serum reacts with the HTLV-III envelope gene product, Western blot analysis was performed. For this analysis, bacterial cell lysates containing recombinant HTLV-III envelope protein were subjected to electrophoresis on an acrylamide gel and the proteins transferred to a nitrocellulose filter using Western blotting technique. Strips of the filter were reacted with 1000-fold diluted rabbit serum (affinity purified) and the antigen-antibody complex formed was detected by incubation of the strips with $^{125}I$-labelled *Staphylocous aureus* protein A followed by autoradiography. Bands were observed corresponding to the envelop protein. The negative controls used were normal bacterial lysates which did not contain HTLV-III expression plasmids. No bands were detected in the latter instance.

What is claimed is:

1. A peptide of the formula

W-X-Lys-Ala-Lys-Arg-Arg-Val-Val-Gln-Arg-Glu-Lys-Arg-Y-Z where W is H-, Cys- or Tyr-, X is a bond or subsequence of one or more amino acids starting from carboxyl terminus of the sequence Asn-Asn-Asn-Asn-Gly-Ser-Glu-Ile-Phe-Arg-Pro-Gly-Gly-Gly-Asp-Met-Arg-Asp-Asn-Trp-Arg-Ser-Glu-Leu-Tyr-Lys-Tyr-Lys-Val-Val-Lys-Ile-Glu-Pro-Leu-Gly-Val-Ala-Pro-Thr, Y is a bond or a sub-sequence of one or more amino acids starting from the amino terminus of the sequence Ala-Val-Gly-Ile-Gly-Ala-Leu-Phe-Leu-Gly-Phe-Leu-Gly-Ala-Ala-Gly-Ser-Thr-Met-Gly-Ala-Ala-Ser-Met-Thr-Leu-Thr-Val-Gln-Ala-Arg-Gln-Leu-Leu-Ser-Gly-Ile-Val-Gln, and Z is -OH, $NH_2$ or -Cys-$NH_2$, provided, however, that one of X or Y is a bond.

2. The peptide of claim 1 where both X and Y are bonds.

3. The peptide of claim 2, wherein W is H- and Z is -Cys-$NH_2$.

4. The peptide of claim 2 wherein W is Cys and Z is -$NH_2$.

5. The peptide of claim 2, wherein W is Tyr-.

6. A peptide of claim 5 labelled with $^{125}I$.

7. The peptide of claim 1 where X is said subsequence and Y is a bond.

8. The peptide of claim 7 where X is Lys-Val-Val-Lys-Ile-Glu-Pro-Leu-Gly-Val-Ala-Pro-Thr.

9. The peptide of claim 8 which is Lys-Val-Val-Lys-Ile-Glu-Pro-Leu-Gly-Val-Ala-Pro-Thr-Lys-Ala-Lys-Arg-Arg-Val-Val-Gln-Arg-Glu-Lys-Arg-Cys-$NH_2$.

10. The peptide of claim 8 which is Tyr-Lys-Val-Val-Lys-Ile-Glu-Pro-Leu-Gly-Val-Ala-Pro-Thr-Lys-Ala-Lys-Arg-Arg-Val-Val-Gln-Arg-Glu-Lys-Arg-Cys-$NH_2$.

11. An immunogen composition comprising a peptide of claim 1, where one of W or Z is Cys covalently bonded to an immunogenic carrier material.

12. The composition of claim 11, wherein said peptide has W as H- and Z as -Cys-$NH_2$.

13. The composition of claim 11, wherein said immunogenic carrier material is keyhole limpet hemocyanin.

14. An antibody which selectively binds to a peptide of the formula

W-X-Lys-Ala-Lys-Arg-Arg-Val-Val-Gln-Arg-Glu-Lys-Arg-Z, where W is H-, Cys- or Tyr-, X is a bond or a subsequence of one or more amino acids starting from carboxyl terminus of the sequence Asn-Asn-Asn-Asn-Gly-Ser-Glu-ILe-Phe-Arg-Pro-Gly-Gly-Gly-Asp-Met-Arg-Asp-Asn-Trp-Arg-Ser-Glu-Leu-Tyr-Lys-Tyr-Lys-Val-Val-Lys-Ile-Glu-Pro-Leu-Gly-Val-Ala-Pro-Thr, and Z is -OH, -$NH_2$ or -Cys-$NH_2$; HTLV-III env protein or an AIDS virus.

15. The antibody of claim 14, which is a polyclonal antibody.

16. The antibody of claim 14 which is a monoclonal antibody.

17. A method of testing human blood for the presence of antibodies to the viral etiological agent of AIDS which comprises:

(a) contacting a peptide of claim 1 which is bound to a solid support with a test sample of human blood, whereby any antibodies to the viral etiological agent of AIDS present in the test sample will bind to the peptide;

(b) removing the test sample;

(c) washing the solid support to remove unbound antibodies;

(d) adding a reagent capable of selectively detecting human antibodies to the washed support step (c), whereby the reagent will bind to any antibodies bound to the support;

(e) washing the support of step (d) to remove unbound reagent; and (f) detecting the bound reagent.

18. The method of claim 17, wherein said solid support is a plastic microtiter plate and said reagent capable of detecting human antibodies is anti-human IgG labelled with horseradish peroxidase which is reacted with a substrate which provides a color change end point in the presence of said peroxidase.

19. The method of claim 17, wherein said peptide is Lys-Val-Val-Lys-Ile-Glu-Pro-Leu-Gly-Val-Ala-Pro-Thr-Lys-Ala-Lys-Arg-Arg-Val-Val-Gln-Arg-Glu-Lys-Arg-Cys-$NH_2$.

20. The method of claim 17, wherein said peptide is Cys-Lys-Ala-Lys-Arg-Arg-Val-Val-Gln-Arg-Glu-Lys-Arg-$NH_2$.

* * * * *